United States Patent [19]
Donahue

[11] Patent Number: 6,110,203
[45] Date of Patent: Aug. 29, 2000

[54] BREAST FORM

[75] Inventor: Linda S. Donahue, Jackson, Mich.

[73] Assignee: Biomedical Horizons Inc., Jackson, Mich.

[21] Appl. No.: 09/009,354

[22] Filed: Jan. 20, 1998

[51] Int. Cl.[7] ................................................ A61F 2/52
[52] U.S. Cl. ........................................................... 623/7
[58] Field of Search ............................ 623/7, 8; 450/7, 450/55, 54

[56] References Cited

U.S. PATENT DOCUMENTS

| | | | |
|---|---|---|---|
| 3,190,292 | 6/1965 | Barnes | 450/55 |
| 3,807,412 | 4/1974 | Connelly | 450/54 |
| 3,845,507 | 11/1974 | Kirby et al. | 450/55 |
| 3,878,568 | 4/1975 | Connelly | 450/54 |
| 4,356,573 | 11/1982 | Knoche | 450/55 |
| 5,480,429 | 1/1996 | Weber-Unger | 623/7 |
| 5,922,023 | 7/1999 | Mulligan et al. | 623/7 |

*Primary Examiner*—David H. Willse
*Assistant Examiner*—Suzette J. Jackson
*Attorney, Agent, or Firm*—Young & Basile, P.C.

[57] ABSTRACT

A breast form prosthesis of the type commonly used in post-mastectomy procedures comprising a soft flexible film envelope having a triangular periphery. The breast form outer surface is of a convex configuration while the inner surface is a concave configuration, the inner and outer surfaces blending at a thin tapered highly flexible periphery. The periphery is substantially planar and projections homogeneously formed of the material of the form located on the inner surface and disposed on opposite sides of the upper peripheral apex having flat surfaces engaging the wearer simultaneously configure the top of the breast form to provide an improved fit and produce a natural appearance.

5 Claims, 1 Drawing Sheet

BREAST FORM

BACKGROUND OF THE INVENTION

1. Field of the Invention

The invention pertains to a breast form prosthesis consisting of an envelope of flexible soft film filled with a silicone material for the purpose of replacing or augmenting breast tissue.

2. Description of the Related Art

Breast form prostheses are commonly used in post-mastectomy situations, and the like, wherein the breast form is placed within a brassiere as to be exteriorly worn next to the patient's chest. Such forms usually consist of an envelope formed of a flexible synthetic film and may be filled with gels, often of a silicone composition, which impart to the form a lifelike consistency, and produce a natural appearance.

It is very important with a breast form prosthesis that as natural a fit as possible be achieved, and previously, breast forms have not conformed to the body to produce as natural an appearance as desired.

OBJECTS OF THE INVENTION

It is an object of the invention to produce a breast form prosthesis which produces a natural appearance and silhouette and closely conforms to the wearer's body.

Yet another object of the invention is to provide a breast form prosthesis having a highly flexible periphery to produce a natural transition between the form and the wearer's body, and wherein the form is configured at its upper regions adjacent the upper form apex to provide an optimum fit and to round out the top of the form.

SUMMARY OF THE INVENTION

In the practice of the invention, a polyurethane outer film is used to form an envelope having a generally triangular configuration having rounded apices. When worn, the three apices defined upper, right and left apexes.

The outer surface of the envelope is of a convex configuration and the inner surface is of a concave shape. The outer and inner surfaces intersect to define the generally triangular periphery, and because of the configuration of the surfaces, the periphery is defined by a highly flexible portion of the form wherein the surfaces intersect at a sharp "point" such that the periphery closely conforms to the wearer's body and produces a natural transition between the wearer and the prosthesis.

In order to provide maximum engagement and fit of the breast form at its upper regions, elongated projections are defined adjacent the periphery between the upper apex and the right and lower apex. Such projections each include a generally flat surface which provide added support and conformity, and these surfaces substantially lie in the plane in which the breast form periphery lies. The use of the projections rounds out the top of the form to improve the fit between the form and the wearer, and assures a natural appearance and silhouette.

The tapered periphery produces a highly flexible form portion adjacent the wearer's body, all of which contribute to the improvements by the invention.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENTS

With reference to the drawings, the breast form prosthesis is represented at 10 and consists of an envelope 11 preferably formed of a soft skin-like synthetic film such as polyurethane. The film is flexible and pleasing to the touch, and the envelope is filled with a soft gel or similar material, usually formed of silicone, having a weight, density and consistency similar to the human breast.

Figure 3:
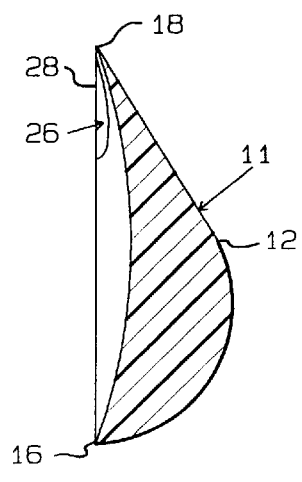
FIG. 3 is an elevational sectional view taken along Section 3—3 of FIG. 2.

The form outer surface 12 is of a convex configuration, as will be appreciated from FIG. 3, and the envelope inner surface 14 is of a concave configuration wherein the surfaces 12 and 14 intersect to provide a tapered periphery 16 which is relatively thin and highly flexible so as to conform to the wearer's body accurately and produce a smooth transition between the body and the prosthesis.

Figure 1:
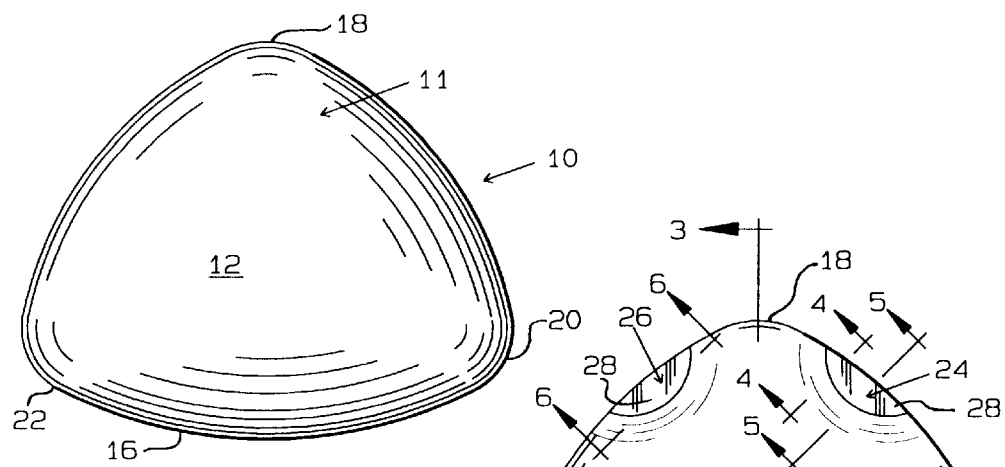
FIG. 1 is a front elevational view of a breast form in accord with the invention.
Figure 2:
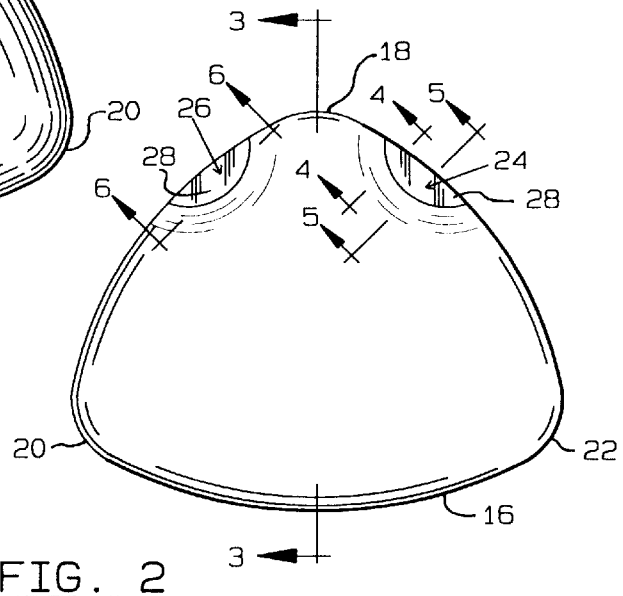
FIG. 2 is a rear elevational view of the form of the invention.

The periphery 16 is generally planar in configuration, and as the envelope is of a triangular form, it includes a rounded upper apex 18, a rounded right apex 20, and a rounded left apex 22, FIG. 1. The tapered configuration of the periphery 16 continues throughout the configuration of the breast form wherein the region adjacent the apices is also flexible and readily conforms to the wearer's body shape.

On the inner surface 14, a pair of projections are defined on the breast form of the material thereof. The projections are formed of the polyurethane material defining the inner surface 14, and are shaped by the inner material of the form. The right projection 24 is located intermediate the upper apex 18 and the right apex 20, and is of an elongated configuration of a length substantially one-third the distance between the centers of the apices 18 and 20. In a similar manner, the left apex 22 is identical having a longitudinal length along the periphery 16 approximately one-third the distance between the center of the apices 18 and 22.

Figure 4:
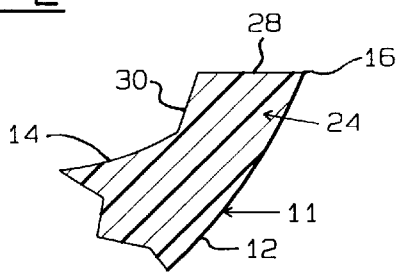
FIG. 4 is a detail enlarged sectional view taken through a projection along Section 4—4 of FIG. 2.
Figure 5:
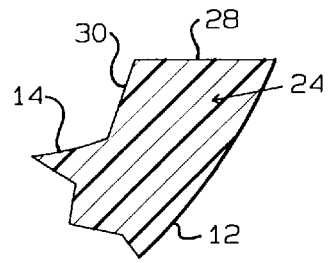
FIG. 5 is an enlarged detail sectional view taken along Section 5—5 of FIG. 2.
Figure 6:
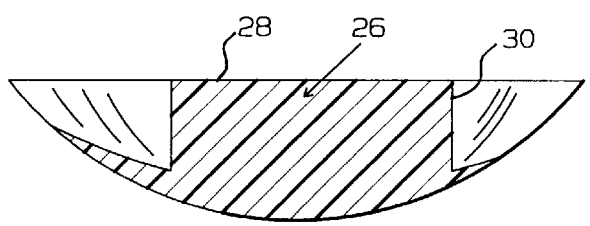
FIG. 6 is an enlarged elevational sectional view taken through a projection along Section 6—6 of FIG. 2.

Each of the projections 24 and 26 are provided with a flat surface 28 substantially coplanar with the plane in which the periphery 16 lies, and in this manner, the projection surfaces 28 are supported by the wearer's body and aid in the conformity of the breast form to the wearer. Each of the projections 24 and 26 includes a wall 30 defining the transition between the surfaces 28 and the form inner surface 24 as will be noted in FIGS. 4–6.

The presence of the projections 24 and 26 rounds out the upper portion of the breast form adjacent the upper apex 18 producing an improved fit at the upper region of the breast form with respect to the wearer's body, and produces a more natural appearance during movement of the wearer. The combination of the configuration of the outer and inner surfaces 12 and 14, the tapered periphery 16 and the projections 24 and 26, together, produce an improved breast form over those presently available closely resembling the natural breast and its movements.

It is appreciated that various modifications to the inventive concepts may be apparent to those skilled in the art without departing from the spirit and scope of the invention.

What is claimed is:

1. A breast form comprising, in combination, an envelope formed of a soft flexible material having a generally triangular peripheral configuration having an upper apex and right and left lower apices, a convex outer surface and a concave inner surface, the improvement comprising, in combination, a pair of elongated projections defined on the envelope concave inner surface extending from the inner surface only adjacent the envelope periphery, a projection being located intermediate the upper apex and the right lower apex and the upper apex and the left lower apex, said projections being adjacent the upper apex and extending along the envelope periphery, each projection being of a length in the direction of the envelope periphery approximately one-third of the peripheral distance between the upper and right apices and between the upper and left apices and formed of the material of the envelope, said projections improving the fit and shape of the breast form to the wearer's body.

2. In a breast form as in claim 1 wherein the envelope periphery substantially lies in a plane, each of said projections including a generally flat surface substantially lying within said plane.

3. In a breast form as in claim 2 wherein said projections are defined by shaped silicone with the envelope.

4. A breast form comprising, in combination, an envelope formed of a soft flexible material having a generally triangular peripheral configuration having an upper apex and right and left lower apices, a convex outer surface and a concave inner surface, the improvement comprising, in combination, the convex outer surface and the concave inner surface converging to define a thin, highly flexible periphery capable of conforming to the wearer's body to form a smooth transition, the envelope periphery substantially lying within a plane, a pair of elongated projections defined on the envelope concave inner surface extending from the inner surface only adjacent the envelope periphery, a projection being located intermediate the upper apex and the right lower apex and the upper apex and the left lower apex, said projections being adjacent the upper apex and extending along the envelope periphery, each projection being of a length in the direction of the envelope periphery approximately one-third of the peripheral distance between the upper and right apices and between the upper and left apices and formed of the material of the envelope, said projections improving the fit and shape of the breast form to the wearer's body.

5. In a breast form as in claim 4, each of said projections including a generally flat surface substantially lying within the envelope plane.

* * * * *